(12) United States Patent
Chan et al.

(10) Patent No.: US 7,094,725 B2
(45) Date of Patent: Aug. 22, 2006

(54) BIPHENYLDIPHOSPHINE COMPOUNDS

(75) Inventors: Albert Sun-Chi Chan, Hung Hom (HK); Liqin Qiu, Hung Hom (HK)

(73) Assignee: The Hong Kong Polytechnic University, Kowloon (HK)

( * ) Notice: Subject to any disclaimer, the term of this patent is extended or adjusted under 35 U.S.C. 154(b) by 7 days.

(21) Appl. No.: 10/888,820

(22) Filed: Jul. 9, 2004

(65) Prior Publication Data

US 2005/0014633 A1    Jan. 20, 2005

Related U.S. Application Data

(60) Provisional application No. 60/486,496, filed on Jul. 11, 2003.

(51) Int. Cl.
*B01J 31/00* (2006.01)
(52) U.S. Cl. ........... 502/150; 502/102; 502/104; 502/152; 502/155; 502/162; 556/13; 556/19; 549/270
(58) Field of Classification Search ........... 502/150, 502/102, 104, 152, 155, 162; 556/13, 19, 556/270
See application file for complete search history.

(56) References Cited

U.S. PATENT DOCUMENTS

| 5,302,738 | A | 4/1994 | Foricher et al. |
| 5,306,834 | A | 4/1994 | Takaya et al. |
| 5,430,191 | A | 7/1995 | Foricher et al. |
| 5,488,172 | A | 1/1996 | Cereghetti et al. |
| 5,600,015 | A | 2/1997 | Broger et al. |
| 6,281,390 | B1 | 8/2001 | Pugin et al. |
| 6,333,291 | B1 | 12/2001 | Yokozawa et al. |
| 6,342,644 | B1 | 1/2002 | Sayo et al. |
| 6,486,337 | B1 | 11/2002 | Burk et al. |
| 6,489,513 | B1 | 12/2002 | Pohl et al. |
| 6,508,753 | B1 | 1/2003 | Burk et al. |
| 6,515,183 | B1 | 2/2003 | Pugin et al. |
| 6,521,769 | B1* | 2/2003 | Zhang ............ 556/19 |
| 6,528,687 | B1 | 3/2003 | Cobley et al. |
| 6,534,657 | B1 | 3/2003 | Zhang |
| 2002/0128501 | A1 | 9/2002 | Zhang |

FOREIGN PATENT DOCUMENTS

| EP | 0 667 350 | 8/1995 |
| WO | WO 92/16536 | 10/1992 |

OTHER PUBLICATIONS

Tang and Zhang, "New Chiral Phosphorus Ligands for Enantioselective Hydrogenation", Chem. Rev. 2003, 103, 3029-3069.*
"Synthesis of a novel chiral biphenyl diphosphine ligand with more chiral centers on the backbone" 224th ACS National Meting, Boston, MA, United States, Aug. 18-22, 2002. (Abstract).
Duprat de Paule et al., "Synthesis and Molecular Modeling Studies of SYNPHOS, a New, Efficient Diphosphane Ligand For Ruthenium-Catalyzed Asymmetric Hydrogenation", Eur. J. Org. Chem., pp. 1931-1941, (2003).
Kitamora et al., "Asymmetric Hydrogenation of 3-oxo Carboxylates using BINAP-Ruthenium Complexes: (R)-(-) methyl 3-hydroxybutanoate (Butanoic acid, 3-hydroxy-, methyl ester, (R)-)", Org. Synth., vol. 71, pp. 1-10, (1993).
Lei et al., "Highly Enantioselective Rh-Catalyzed Intramolecular Alder-Ene Reactions for the Syntheses of Chiral Tetrahydrofurans", Angew. Chem. Int. Ed., vol. 41, No. 18, pp. 3457-3460, (2002).
Mashima et al., "Cationic BINAP-Ru(II) Halide Complexes: Highly Efficient Catalysts for Stereoselective Asymmetric Hydrogenation of α- and β-Functionalized Ketones", J. Org. Chem., vol. 59, pp. 3064-3076, (1994).

(Continued)

*Primary Examiner*—J. A. Lorengo
*Assistant Examiner*—Jennine Brown
(74) *Attorney, Agent, or Firm*—John W. Kung

(57) ABSTRACT

The present invention provides compounds of the formula

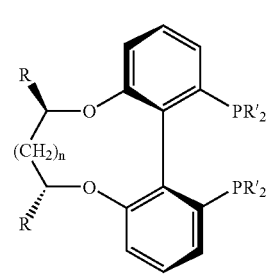

(I)

wherein
  R is optionally substituted lower alkyl, cycloalkyl or aryl;
  R' is alkyl or aryl;
  n is zero or an integer of 1 or 2;
or an enantiomer thereof; or an enantiomeric mixture thereof.

The compounds of formula (I) are bridged $C_2$-symmetric biphenyldiphosphine analogs and, thus, may be employed as ligands to generate chiral transition metal catalysts which may be applied in a variety of asymmetric reactions. The compounds of the present invention are easily accessible in high diastereomeric and optical purity according to the methods disclosed herein.

35 Claims, No Drawings

OTHER PUBLICATIONS

Noyori et al., "BINAP: An Efficient Chiral Element for Asymmetric Catalysis", Acc. Chem. Res., vol. 23, pp. 345-350, (1990).

Ohkuma et al., "Asymmetric Hydrogenation of Alkenyl Cyclopropyl, and Aryl Ketones. RuCl$_2$(xylbinap)(1,2-diamine) as a Precatalyst Exhibiting a Wide Scope", J. Am. Chem. Soc., vol. 120, pp. 13529-13530, (1998).

Qui et al., "Remarkably diastereoselective synthesis of a chiral biphenyl diphosphine ligand and its application in asymmetric hydrogenation", PNAS, vol. 101, No. 16, pp. 5815-5820, (Apr. 20, 2004).

Qiu, Liqin, "Highly Efficient Asymmetric Synthesis of Novel Diphosphine Ligands with Additional Chiral Centers on the Backbone and Their Applications in Asymmetric Hydrogenation Reactions", The Hong Kong Polytechnic University, (Jan. 2003).(Thesis).

Saito et al., "New Chiral Diphosphine Ligands Designed to Have a Narrow Dihedral Angle in the Biaryl Backbone", Adv. Synth. Catal. vol. 343, No. 3, pp. 264-267, (2001).

Schmid et al., "Axially Dissymmetric Diphosphines in the Biphenyl Series: Synthesis of (6,6'-Dimethoxybiphenyl-2,2'-diyl)bis(diphenylphosphine) ('MeO-BIPHEP') and Analogues via an ortho-Lithiation/Iodination Ullmann-Reaction Approach", Helvetica Chimica Acta, vol. 74, pp. 370-389, (1991).

Schmid et al., "New Developments in enantioselective hydrogenation", Pure & Appl. Chem., vol. 68, No. 1, pp. 131-138 (1996).

Wu et al., "Highly Enantioselective Hydrogenation of Enol Acetates Catalyzed by Ru-TunaPhos Complexes", Organic Letters, vol. 4, No. 25, pp. 4495-4497, (2002).

Zhang et al., "Synthesis of Chiral Bisphosphines with Tunable Bite Angles and Their Applications in Asymmetric Hydrogenation of β-Ketoesters", J. Org. Chem, vol. 65, pp. 6223-6226, (2000).

* cited by examiner

BIPHENYLDIPHOSPHINE COMPOUNDS

This application claims the benefit of U.S. Provisional Application No. 60/486,496, filed Jul. 11, 2003.

BACKGROUND OF THE INVENTION

Asymmetric catalysis is one of the most powerful methods for accessing a wide range of enantiomerically enriched compounds through the action of a chiral catalyst in a variety of asymmetric reactions. Highly promising candidates for asymmetric synthesis are transition metal complexes bearing chiral ligands. Despite the large number of chiral ligands employed in asymmetric synthesis, only a few have found a practical application in the manufacture of chiral molecules by the chemical and pharmaceutical industry.

Among these ligands, BINAP is one of frequently used chiral ligands. BINAP has been shown to be highly effective for many asymmetric reactions (Noyori and Takaya, *Acc. Chem. Res.,* 1990, 23, 345; and Olkuma et al., *Am. Chem. Soc.,* 1998, 120, 13529). Related axially dissymmetric ligands, such as MeO-BIPHEP and BIPHEMP have also been employed in a number of asymmetric reactions (Schmid et al., *Pure & Appl. Chem.,* 1996, 68, 131; Foricher, Heiser and Schmid, U.S. Pat. No. 5,302,738; Michel, European Patent Application 0667350 A1; and Broger et al., PCT WO 92/16536). The structures for BINAP, BIPHEMP and MeO-BIPHEP are illustrated in FIG. 1.

FIG. 1.

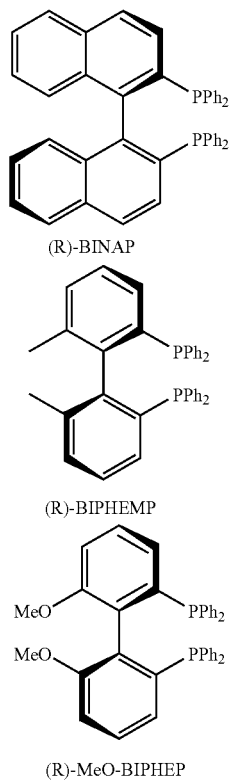

Despite the extensive research in this area, there are still a variety of reactions in which only modest enantioselectivity has been achieved with these ligands. Thus, it remains highly desirable to develop novel chiral ligands which are selective and effective in a variety of asymmetric catalytic reactions, and are synthetically easily accessible.

SUMMARY OF THE INVENTION

The present invention provides compounds of the formula

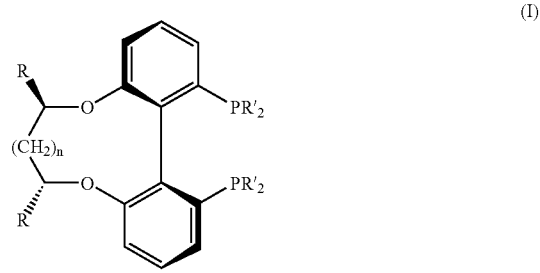

(I)

wherein
R is optionally substituted lower alkyl, cycloalkyl or aryl;
R' is alkyl or aryl;
n is zero or an integer of 1 or 2;

or an enantiomer thereof; or an enantiomeric mixture thereof.

The compounds of formula (I) are bridged $C_2$-symmetric biphenyldiphosphine analogs and, thus, may be employed as ligands to generate chiral transition metal catalysts which may be applied in a variety of asymmetric reactions. The compounds of the present invention are easily accessible in high diastereomeric and enantiomeric purity according to the methods disclosed herein.

Other objects, features, advantages and aspects of the present invention will become apparent to those skilled in the art from the following description and appended claims. It should be understood, however, that the following description, appended claims, and specific examples, while indicating preferred embodiments of the invention, are given by way of illustration only. Various changes and modifications within the spirit and scope of the disclosed invention will become readily apparent to those skilled in the art from reading the following.

DETAILED DESCRIPTION OF THE INVENTION

Listed below are definitions of various terms used to describe the compounds of the present invention. These definitions apply to the terms as they are used throughout the specification unless they are otherwise limited in specific instances either individually or as part of a larger group.

The term "optionally substituted alkyl" refers to unsubstituted or substituted straight- or branched-chain hydrocarbon groups having 1–20 carbon atoms, preferably 1–7 carbon atoms. Exemplary unsubstituted alkyl groups include methyl, ethyl, propyl, isopropyl, n-butyl, t-butyl, isobutyl, pentyl, neopentyl, hexyl, isohexyl, heptyl, octyl and the like. Substituted alkyl groups include, but are not limited to, alkyl groups substituted by one or more of the following groups: halo, cycloalkyl, alkoxy or aryl.

The term "lower alkyl" refers to those optionally substituted alkyl groups as described above having 1–7, preferably 1–5 carbon atoms.

The term "alkoxy" refers to alkyl-O—.

The term "halogen", "halide" or "halo" refers to fluorine, chlorine, bromine and iodine.

The term "cycloalkyl" refers to optionally substituted monocyclic aliphatic hydrocarbon groups of 3–6 carbon atoms, which may be substituted by one or more substituents, such as alkyl, alkoxy or halo.

Exemplary monocyclic hydrocarbon groups include, but are not limited to, cyclopropyl, cyclobutyl, cyclopentyl, cyclohexyl and the like.

The term "aryl" refers to a phenyl group, which may optionally be substituted by 1–4 substituents, such as optionally substituted alkyl, cycloalkyl, halo or alkoxy.

As described herein above, the present invention relates to compounds of formula (I), to methods for their preparation, and to use of such compounds in asymmetric catalysis.

Preferred are the compounds of formula (I) wherein
R is methyl, ethyl, n-propyl, i-propyl, n-butyl, i-butyl, neopentyl, cyclopropyl, benzyl or phenyl;
R' is phenyl;
n is zero or an integer of 1 or 2;

or an enantiomer thereof; or an enantiomeric mixture thereof.

Further preferred are the compounds of formula (I) wherein
R is methyl;
R' is phenyl;
n is zero or an integer of 1 or 2;

or an enantiomer thereof; or an enantiomeric mixture thereof.

Particular embodiments of the invention are:
(S)-[6,6'-(2R,4R-pentadioxy)]-(2,2')-bis(diphenylphosphino)-(1,1')-biphenyl, also designated as Ligand A;
(S)-[6,6'-(2R,5R-hexadioxy)]-(2,2')-bis(diphenylphosphino)-(1,1')-biphenyl, also designated as Ligand B; and
(R)-[6,6'-(2S,3S-butadioxy)]-(2,2')-bis(diphenylphosphino)-(1,1')-biphenyl, also designated as Ligand C.

The compounds of the present invention preferably have an optical purity of at least 85% enantiomeric excess (ee), more preferably at least 95% ee, and most preferably at least 98% ee.

The compounds of the present invention may be employed to generate a chiral transition metal catalyst comprising a suitable transition metal bound to a compound of the formula

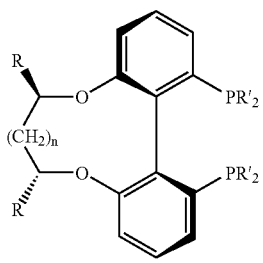

(I)

wherein
R is optionally substituted lower alkyl, cycloalkyl or aryl;
R' is alkyl or aryl;
n is zero or an integer of 1 or 2;

or an enantiomer thereof; or an enantiomeric mixture thereof.

Particularly useful are the catalysts of the present invention wherein the transition metal is bound to a compound of formula (I) wherein
R is methyl, ethyl, n-propyl, i-propyl, n-butyl, i-butyl, neopentyl, cyclopropyl, benzyl or phenyl;
R' is phenyl;
n is zero or an integer of 1 or 2;

or an enantiomer thereof; or an enantiomeric mixture thereof.

Especially useful are the catalysts of the present invention wherein the transition metal is bound to a compound of formula (I) wherein
R is methyl;
R' is phenyl;
n is zero or an integer of 1 or 2;

or an enantiomer thereof; or an enantiomeric mixture thereof.

Suitable transition metals for the catalyst system of the present invention include, but are not limited to, copper (Cu), iridium (Ir), nickel (Ni), palladium (Pd), platinum (Pt), rhodium (Rh) and ruthenium (Ru).

Particularly useful are the catalysts of the present invention wherein the transition metal is selected from the group consisting of copper, iridium, nickel, palladium, platinum, rhodium and ruthenium, and the transition metal is bound to a compound of formula (I) wherein
R is methyl, ethyl, n-propyl, i-propyl, n-butyl, i-butyl, neopentyl, cyclopropyl, benzyl or phenyl;
R' is phenyl;
n is zero or an integer of 1 or 2;

or an enantiomer thereof; or an enantiomeric mixture thereof.

Especially useful are the catalysts of the present invention wherein the transition metal is selected from the group consisting of copper, iridium, nickel, palladium, platinum, rhodium and ruthenium, and the transition metal is bound to a compound of formula (I) wherein
R is methyl;
R' is phenyl;
n is zero or an integer of 1 or 2;

or an enantiomer thereof; or an enantiomeric mixture thereof.

Especially effective are the catalysts of the present invention wherein the transition metal is ruthenium or rhodium, and the transition metal is bound to a compound of formula (I) wherein
R is methyl;
R' is phenyl;
n is zero or an integer of 1 or 2;

or an enantiomer thereof; or an enantiomeric mixture thereof.

The compounds of the present invention may be prepared by reacting a phenol of the formula

(II)

wherein X is chloro, bromo or iodo, preferably bromo; with an alkylating agent of the formula

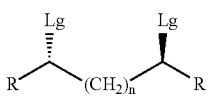

wherein Lg represents a leaving group, such as p-toluenesulfonate or methanesulfonate; and R and n have meanings as defined herein; or an enantiomer thereof; or an enantiomeric mixture thereof; in the presence of a base, such as potassium or cesium carbonate, and an inert organic solvent, such as tetrahydrofuran (THF), N,N-dimethylformamide (DMF), N-methylpyrrolinone (NMP) or dimethylsulfoxide (DMSO), preferably DMSO, to afford a compound of the formula

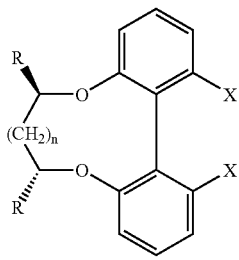

wherein R, n and X have meanings as defined herein; or an enantiomer thereof; or an enantiomeric mixture thereof. Preferably, the alkylation reaction is carried out at room temperature (RT).

Alkylating agents of formula (III) may be obtained as described herein in the Examples, or according to methods well known in the art. Preferably, the alkylating agents of formula (III) have an optical purity of at least 85% ee, more preferably at least 95% ee, and most preferably at least 98% ee.

A compound of formula (IV) may then be dehalogenated via halogen metal exchange, e.g., by treatment with an organometallic reagent, such as t-butyllithium or n-butyllithium, in an inert organic solvent, such as THF or hydrocarbon solvent, e.g., pentane or hexane, or a mixture of solvents thereof, followed by treatment of the resulting dianion with a phosphine chloride of the formula

wherein R' is alkyl or aryl; to afford a compound of the formula

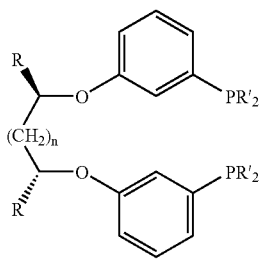

wherein R, n and R' have meanings as defined herein; or an enantiomer thereof; or an enantiomeric mixture thereof. The halogen metal exchange reaction may be conducted at a temperature ranging from about −100° C. to about −45° C., preferably at about −78° C.

A compound of formula (VI) may then be treated with an oxidizing agent, such as manganese dioxide, ozone, potassium peroxysulfate or hydrogen peroxide, preferably hydrogen peroxide, in an organic solvent, such as dichloromethane (DCM) or acetone, preferably acetone, to afford a compound of the formula

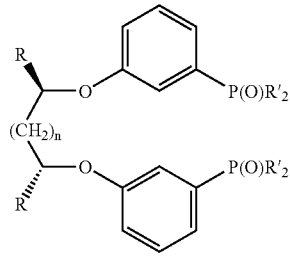

wherein R, n and R' have meanings as defined above; or an enantiomer thereof; or an enantiomeric mixture thereof. The oxidation may be carried out at a temperature ranging from about −15° C. to RT, preferably at about 0° C.

A compound of formula (VII) may then be deprotonated selectively at a position between the substituents, e.g., by treatment with a strong base, such as lithium diisopropylamide (LDA), in an inert organic solvent, such as THF, followed by treatment of the resulting dianion with molecular iodine, or an iodine source thereof, e.g., diiodoethane, to afford a compound of the formula

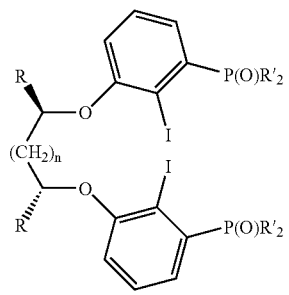

wherein R, n and R' have meanings as defined above; or an enantiomer thereof; or an enantiomeric mixture thereof. The deprotonation reaction may be conducted at a temperature ranging from about −100° C. to about −45° C., preferably at about −78° C.

A compound of formula (VIII) may be converted to a compound of formula (IX) under conditions of Ullmann coupling, e.g., a compound of formula (VIII) may be treated with copper in an inert organic solvent, such as DMF or DMSO; to afford a compound of the formula

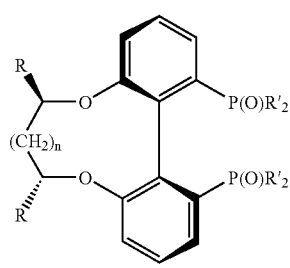

wherein R, n and R' have meanings as defined above; or an enantiomer thereof; or an enantiomeric mixture thereof. The intramolecular coupling reaction is preferably conducted at a temperature ranging from about 100° C. to about 170° C., preferably at about 140° C.

Finally, a compound of formula (IX) may be treated with a reducing agent, such as trichlorosilane in the presence of a tertiary amine, such as tri-n-butylamine, in an inert organic solvent, such as toluene, to afford a compound of formula (I) wherein R, n and R' have meanings as defined above; or an enantiomer thereof; or an enantiomeric mixture thereof.

The intramolecular Ullmann coupling employed herein for the preparation of compounds of formula (I) represents a rare example of a complete substrate-directed asymmetric induction by means of Ullmann coupling. The central chirality is translated into axial chirality with high efficiency, from which only one atropdiastereomer is obtained.

Alternatively, the compounds of the present invention may be prepared by reacting a compound of the formula

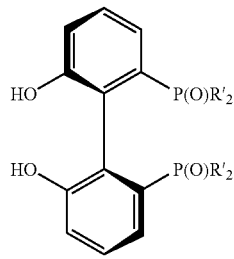

(X)

wherein R' has a meaning as defined above; or an enantiomer thereof; or an enantiomeric mixture thereof; with an alkylating agent of the formula

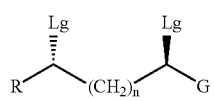

(III)

wherein Lg represents a leaving group as defined herein above; and R and n have meanings as defined above; or an enantiomer thereof; or an enantiomeric mixture thereof; in the presence of a base, such as potassium or cesium carbonate, and an inert organic solvent, such as THF, DMF, NMP or DMSO, preferably DMF; to afford a compound of the formula

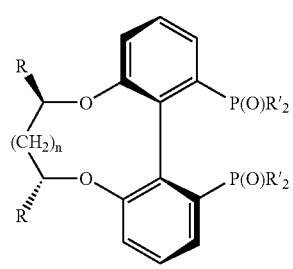

(IX)

wherein R, n and R' have meanings as defined above; or an enantiomer thereof; or an enantiomeric mixture thereof. The ring closure reaction may be conducted at a temperature ranging from about 20° C. to about 90° C., preferably at about 55° C.

Compounds of formula (X) may be obtained analogously as described by Schmid et al. in *Helv. Chim. Acta,* 1991, 74, 370. Preferably, compounds of formula (X) have an optical purity of at least 85% ee, more preferably at least 95% ee, and most preferably at least 98% ee.

Compounds of formula (IX) may then be converted to the compounds of the present invention as described herein previously.

The ring closure reaction employed herein for the preparation of compounds of formula (I) proceeds with a precise chiral recognition directed by the stereochemistry of the alkylating agent, from which only one atropdiastereomer is obtained.

The compounds of formula (I) may then be converted to chiral transition metal catalysts of the present invention by reacting a compound of formula (I), or an enantiomer thereof, or an enantiomeric mixture thereof, with a suitable transition metal salt, or a complex thereof, to afford a catalyst of the present invention. The choice of a suitable transition metal salt, or a complex thereof, is generally known to those skilled in the art and depends on the nature of the asymmetric reaction to be performed. A suitable transition metal salt, or a complex thereof, for the preparation of a catalyst of the present invention may be selected from those described herein in the illustrative Examples. Further examples of such transition metal salts may be found, e.g., in Seyden-Penne, *"Chiral Auxiliaries and Ligands in Asymmetric Synthesis"*, John Wiley & Sons, Inc., NY (1995). A catalyst of the present invention may be generated in situ, or it may be isolated prior to use.

The catalysts of the present invention obtainable as described herein may be employed for converting a prochiral substrate to a chiral product under reaction conditions otherwise suitable for asymmetric induction.

Such asymmetric reactions include, but are not limited to, catalytic hydrogenation, hydrosilylation, hydroboration, hydroformylation, hydrocarboxylation, hydroacylation, Heck reaction and some allylic isomerization and substitution reactions. A preferred reaction for asymmetric induction using a chiral catalyst of the present invention is catalytic hydrogenation. The catalysts of the present invention are especially effective when employed in asymmetric catalytic hydrogenation of ketones, e.g., α- and β-ketoesters, and activated carbon-carbon double bonds such as α,β-unsaturated carboxylic acids, e.g., 2-(6'-methoxy-2'-naphthyl)propenoic acid, β-(acylamino)acrylates and enol acetates.

As exemplified in Table 1 for asymmetric catalytic hydrogenation of β-ketoesters, the catalysts of the present invention, in particular, a catalyst comprising ruthenium and Ligand A, Ligand B or Ligand C, compare favorably to well known MeO-BIPHEP and BINAP ligands under otherwise identical reaction conditions.

TABLE 1

$$R^1 \underset{R^2}{\overset{O \quad O}{\parallel \quad \parallel}} OR^3 \xrightarrow[H_2]{RuLCl_2(DMF)_n} R^1 \underset{R^2}{\overset{OH \quad O}{\underset{*}{\parallel}}} OR^3$$

| Entry | R¹ | R² | R³ | Ligand C | Ligand A | Ligand B | (S)-MeO-BIPHEP | (S)-BINAP |
|---|---|---|---|---|---|---|---|---|
| | | | | % ee (configuration)[a] | | | | |
| 1[b] | Me | H | Me | 99.3 (R) | 97.5 (S) | 98.9 (S) | 97.7 (S) | 97.7 (S) |
| 2[b] | Me | H | Et | 99.4 (R) | 98.5 (S) | 98.9 (S) | 98.0 (S) | 98.0 (S) |
| 3[b] | Me | H | CH₂Ph | 99.3 (R) | 98.5 (S) | 99.1 (S) | 98.1 (S) | 96.1 (S) |
| 4[b] | ClCH₂ | H | Et | 97.2 (S) | 96.2 (R) | 96.3 (R) | 95.5 (R) | 94.2 (R) |
| 5[b] | Ph | H | Et | 95.6 (S) | 96.6 (R) | 95.4 (R) | 93.0 (R) | 89.3 (R) |
| 6[c] | Ph | Cl | Et | 92.7 (22.0% anti; 2R, 3R) | 94.6 (27.5% anti; 2S, 3S) | 73.1 (14.5% anti; 2S, 3S) | 70.8 (16.0% anti; 2S, 3S) | 16.3 (10.4% anti; 2S, 3S) |
| | | | | 26.2 (78.0% syn; 2S, 3R) | 37.1 (72.5% syn; 2R, 3S) | 6.5 (85.5% syn; 2R, 3S) | 5.3 (84.0% syn; 2R, 3S) | 9.8 (89.6% syn; 2R, 3S) |

[a]Reaction time = 24 h except for entry 5 (100 h); substrate/[Ru] = 667:1 (mol:mol) except for entry 6 substrate/[Ru] = 100:1; reactions are carried out at 70° C. except for entry 6 (RT) and entry 4 (optimum temperature from 70–100° C.); H₂ pressure = 50 psi except for entry 6 (1000 psi); complete conversions are obtained in all cases.
[b]The ee values are determined by chiral GC with a WCOT fused silica CP Chirasil-DEX CB column (25 m × 0.25 mm) after converting the products to the corresponding acetyl derivatives.
[c]The ee values are determined by chiral HPLC with a Daicel Chiralcel OD column. The ratio of anti to syn products is determined by ¹H NMR.

Similarly, as illustrated in Table 2, a catalyst of the present invention, e.g., a catalyst comprising ruthenium and Ligand C, is much more active and enantioselective than the corresponding BINAP derived catalyst in the hydrogenation of α-ketoesters. For instance, the hydrogenation of methyl benzoylformate using Ligand C as the ligand is completed in 15 h at 40 atm and RT giving the product in 97.0% ee. In contrast thereto, when BINAP is employed as the ligand, 94 h is required to complete the reaction at 100 atm hydrogenation pressure and 30° C. yielding the product only in 79.0% ee.

TABLE 2

$$Ph \underset{O}{\overset{O}{\parallel}} \underset{}{\overset{}{\parallel}} OMe \xrightarrow[H_2, MeOH]{[RuL(\eta^6-C_6H_6)Cl]Cl} Ph \underset{OH}{\overset{O}{\underset{*}{\parallel}}} OMe$$

| Ligand | S/C[b] | T (° C.) | P_H2 (atm) | Time (h) | % ee (configuration)[a] |
|---|---|---|---|---|---|
| Ligand C | 600 | 60 | 35 | 15 | 93.5 (R) |
| Ligand C | 600 | RT | 75 | 15 | 95.7 (R) |
| Ligand C | 600 | RT | 40 | 15 | 97.0 (R) |
| (S)-BINAP | 560 | 30 | 100 | 94 | 79.0 (S) |

[a]The ee values are determined by chiral GC with a Lipodex-A (50 m × 0.25 mm); all conversions are more than 99%.
[b]Refers to the molar ratio of the substrate to the catalyst.

Yet another example of the effectiveness of the catalyst system of the present invention is illustrated in Table 3, i.e., asymmetric catalytic hydrogenation of 2-(6'-methoxy-2'-naphthyl)propenoic acid employing a catalyst of the present invention comprising ruthenium and Ligand A, Ligand B or Ligand C. The data in Table 3 clearly shows that the enantiofacial recognition abilities and reactivity of the catalytic systems prepared with Ligand A, Ligand B and Ligand C are again comparable to well known Ru(BINAP) and Ru(MeO-BIPHEP) systems. Interestingly, reaction hydrogen pressure has little influence on the enantioselectivity when (S)-MeO-BIPHEP is used as the ligand, whereas, the influence is more significant for the ligands of the present invention, i.e., increase of hydrogen pressure leads to higher enantioselectivities.

TABLE 3

[Reaction scheme: methoxy-naphthyl acrylic acid → methoxy-naphthyl propanoic acid (naproxen) using Ru[L(p-cymene)Cl]Cl, H₂]

| Entry | $P_{H2}$ (psi) | T (°C.) | Time (h) | Ligand C | Ligand A | Ligand B | (S)-MeO-BIPHEP | (S)-BINAP |
|---|---|---|---|---|---|---|---|---|
| | | | | \multicolumn{5}{c}{% ee (configuration)[a,b]} |
| 1 | 500 | RT | 4 | 85.8 (R) | 87.5 (S) | 85.7 (S) | 88.3 (S) | 86.6 (S) |
| 2 | 1000 | RT | 4 | 89.5 (R) | 88.7 (S) | 88.4 (S) | 89.3 (S) | 89.0 (S) |
| 3 | 1500 | RT | 4 | 91.2 (R) | 90.4 (S) | 89.5 (S) | 89.5 (S) | 89.7[c] (S) |
| 4 | 1000 | RT | 0.5 | 89.3 (98.5%, R) | 88.8 (100%, S) | 88.3 (100%, S) | 89.3 (100%, S) | 89.0 (90.0%, S) |
| 5 | 1000 | 0 | 24 | 95.2 (R) | 94.6 (S) | 95.0 (S) | 94.2 (S) | 94.1 (S) |
| 6 | 1500 | 0 | 24 | 96.0 (R) | 95.1 (S) | 95.4 (S) | 94.4 (S) | — |

[a]Reaction conditions: substrate/catalyst = 100:1 (mol/mol); complete conversions are obtained in all cases except in entry 4.
[b]The ee values are determined by chiral HPLC with a Sumichiral OA-2500 column.
[c]Reaction pressure = 1600 psi.

Furthermore, as illustrated in Table 4, a catalyst of the present invention, e.g., a catalyst comprising ruthenium and Ligand C, may be employed for the preparation of optically active β-amino acids in good to excellent enantioselectivity by asymmetric hydrogenation of β-(acylamino)acrylates. Optimization studies indicate that methanol (MeOH) may be the best solvent for this catalyst system. The hydrogen pressure has little influence on the enantioselectivity, however, lower reaction temperatures afford higher enantioselectivities at the expense of the reaction rate. As exemplified in Table 4, good to excellent enantioselectivities are achieved in the asymmetric hydrogenation of (E)-β-alkyl-substituted β-(acetylamino)acrylates when a catalyst comprising Ligand C is employed, and substrates with a bulky β-alkyl substituent give the best ee's (up to 99.8%, entry 11).

TABLE 4

[Reaction scheme: $R^1$-substituted β-(acetylamino)acrylate → β-amino ester using [RuL(η⁶-C₆H₆)Cl]Cl, H₂, MeOH]

| Entry[a] | $R^1$ | $R^2$ | T (° C.) | Time (h) | % ee[b] |
|---|---|---|---|---|---|
| 1 | Me | Me | RT | 6 | 96.4 |
| 2 | Me | Me | 0 | 48 | 97.7 |
| 3 | Me | Et | RT | 6 | 95.7 |
| 4 | Me | Et | 0 | 48 | 98.1 |
| 5 | Et | Me | RT | 6 | 94.8 |
| 6 | Et | Me | 0 | 48 | 96.9 |
| 7 | i-Pr | Me | RT | 6 | 93.5 |
| 8 | i-Pr | Me | 0 | 48 | 98.8 |

TABLE 4-continued

| Entry[a] | $R^1$ | $R^2$ | T (° C.) | Time (h) | % ee[b] |
|---|---|---|---|---|---|
| 9 | n-Pr | Et | RT | 6 | 94.0 |
| 10 | n-Pr | Et | 0 | 48 | 96.0 |
| 11 | t-Bu | Me | RT | 6 | 99.8 |

[a]Reaction conditions: 1.7 mg substrate; substrate/catalyst = 100 (mol/mol); substrate concentration = 0.5–0.09 M in MeOH, $P_{H2}$ = 250 psi; the conversions are determined by NMR and GC analysis and were found to be higher than 99.9% in all cases.
[b]The ee values are determined by chiral GC with a 25 m × 0.25 mm Chirasil-DEX CB column or 30 m × 0.25 mm γ-DEX-225 column; all products are in the S-configuration.

Finally, a catalyst of the present invention, e.g., a catalyst comprising ruthenium and Ligand C, may be employed in the asymmetric hydrogenation of enol acetates which is an attractive alternative to the direct hydrogenation of unfunctionalized ketones. As illustrated in Table 5, the asymmetric hydrogenation of enol acetates using a catalyst system comprising Ligand C provides the corresponding chiral acetates in good to excellent enantioselectivity. During optimization of the reaction conditions a strong solvent effect is revealed. The best ee's may be achieved when a mixture of ethanol (EtOH) and DCM (4:1) is used.

TABLE 5

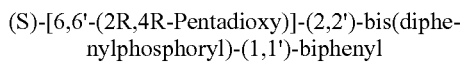

| Entry | Ar | T (° C.) | Time (h) | Conv, % | % ee[b] |
|---|---|---|---|---|---|
| 1 | Naphthyl | RT | 12 | >99 | 96.7 |
| 2 | p-FC$_6$H$_4$ | RT | 12 | >99 | 97.1 |
| 3 | p-ClC$_6$H$_4$ | RT | 14 | >99 | 96.5 |
| 4 | p-MeOC$_6$H$_4$ | 50 | 48 | >99 | 92.6 |
| 5 | C$_6$H$_5$ | 50 | 96 | 75 | 94.9 |

[a]Reaction conditions: EtOH/DCM (4:1) is used as the solvent; substrate/Ru = 100:1; P$_{H2}$ = 50 psi.
[b]The ee values are determined by chiral GC with a Varian 25 m × 0.25 mm CP-CYCLODEX B 236 M column; all products are in the R-configuration.

As the data described herein above indicates, among the catalysts of the present invention comprising ruthenium and Ligand A, Ligand B or Ligand C, the highest enantioselectivities are generally obtained with Ligand C of the smallest dihedral angle and the largest rigidity.

The following Examples are intended to further illustrate the invention and are not to be construed as being limitations thereon. If not mentioned otherwise, all evaporations are performed under reduced pressure, preferably between about 5 and 50 mmHg. The structure of final products, intermediates and starting materials is confirmed by standard analytical methods, e.g., microanalysis, melting point, and spectroscopic characteristics, e.g., MS, IR, NMR. Abbreviations used are those conventional in the art. The concentration for [α]$_D$ determinations is expressed in mg/mL.

Unless otherwise noted, all reactions are carried out under an inert atmosphere of dry nitrogen and are followed by TLC. Glassware is flame dried before use. Standard syringe techniques are applied to transfer dry solvents and reagents. The preparation of samples and the setup of high-pressure reactor are either carried out in a nitrogen-filled continuously purged MBRAUN Model lab master 230 glovebox or using standard Schlenk-type techniques. $^1$H NMR, $^{31}$P NMR and $^{13}$C NMR spectra are recorded on a Varian 500 spectrometer (500, 202 and 125 MHz respectively). Chemical shifts (δ) are given in ppm and are referenced to residual solvent peaks ($^1$H NMR, $^{13}$C NMR) or to an external standard (85% H$_3$PO$_4$, $^{31}$P NMR). High resolution mass measurements are carried out with a VG MICROMASS, Fison VG platform, or a Finnigan Model Mat 95 ST instrument. Optical rotations are recorded on a Perkin-Elmer 341 polarimeter in a 10 cm cell. Enantiomeric excesses of the asymmetric hydrogenation products are determined by chiral GC and HPLC. HPLC analyses are performed using a Waters Model 600 with a Waters 486 UV detector. Gas chromatographic analyses are performed on an HP 4890A GC with an FID detector. THF and toluene are freshly distilled from sodium/benzophenone ketyl, while DMSO, DMF, DCM, and Bu$_3$N are distilled from CaH$_2$ under nitrogen atmosphere. MeOH and EtOH are distilled from magnesium under nitrogen atmosphere. All other chemicals are used as received from Aldrich, Acros or Strem without further purification. All substrates used in moisture-sensitive reactions are pre-dried twice with toluene azeotrope prior to use.

EXAMPLE 1

(S)-[6,6'-(2R,4R-Pentadioxy)]-(2,2')-bis(diphenylphosphoryl)-(1,1')-biphenyl

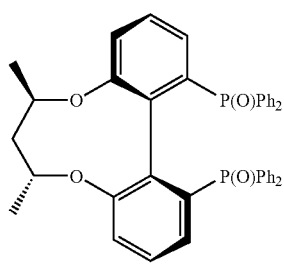

A. (2S,4S)-Pentanediol di-p-tosylate

Under N$_2$ atmosphere and at 0° C., a solution of p-toluenesulfonyl chloride (19.3 g, 101.0 mmol) in 50 mL of DCM is added slowly into a mixture of (2S,4S)-pentanediol (5.0 g, 48.0 mmol) and TEA (14.0 mL, 101.0 mmol) in 50 mL of DCM over a period of 4 h. The reaction temperature is kept at 0° C. for 2 h, then is raised to RT and the reaction is continued overnight. The resultant solution is concentrated in vacuo to give a crude product. Purification by re-crystallization in methanol affordes (2S,4S)-pentanediol di-p-tosylate as colorless crystals: $^1$H NMR (CDCl$_3$) 500 MHz δ 1.19 (d, J=6.5 Hz, 6H), 1.84 (t, J=6 Hz, 2H), 2.42 (s, 6H), 4.65–4.71 (m, 2H), 7.32 (d, J=8.5 Hz, 4H), 7.76 (d, J=8.5 Hz, 4H); $^{13}$C NMR (CDCl$_3$) 125 MHz δ 21.18, 21.51, 43.75, 76.67, 127.58, 129.73, 134.12, 144.64; [α]$^{20}_D$=+16.0° (c=1, CHCl$_3$).

B. (2R,4R)-2,4-bis(3-Bromophenoxy)pentane

Under N$_2$ atmosphere and at RT, a mixture of 3-bromophenol (0.746 g, 4.3 mmol) and K$_2$CO$_3$ (1.192 g, 8.6 mmol) in DMSO (5 mL) is stirred for 1 h, then a solution of the title A compound, (2S,4S)-pentanediol di-p-tosylate (0.8893 g, 2.2 mmol) in DMSO (10 mL) is added dropwise into this mixture over a period of 4 h. The mixture is continuously stirred at RT for 48 h before pouring into water (100 mL). The organic phase is diluted with DCM, washed with 2 N aqueous HCl (10 mL), water and brine. The organic layer is separated, dried over anhydrous Na$_2$SO$_4$ and concentrated in vacuo. The residue is purified through a silica gel column (elutent:EtOAc/hexane=5/100) to give (2R,4R)-2,4-bis(3-bromo-phenoxy)pentane as a colorless oil: $^1$H NMR (CDCl$_3$) 500 MHz δ 1.30–1.31 (d, J=6 Hz, 6H), 1.94–1.97 (dd, J=5.5 Hz, 7 Hz, 2H), 4.55–4.61 (m, 2H), 6.72–6.75 (m, 2H), 6.96–7.06 (m, 6H); $^{13}$C NMR (CDCl$_3$) 125 MHz δ 20.06, 44.76, 71.07, 114.74, 119.44, 122.82, 123.92, 130.51, 158.83; MS (EI+VE+LMR) calcd for C$_{17}$H$_{18}$Br$_2$O$_2$ [M]$^+$ 414.1, found 414.0; HRMS (EI+VE+LMR) calcd for C$_{17}$H$_{18}$Br$_2$O$_2$ [M]$^+$ 411.9674, found 411.9726; [α]$^{20}_D$=−77.2° (c=1, hexane).

C. (2R,4R)-2,4-bis[3-(Diphenylphosphoryl)phenoxy]pentane

The title B compound, (2R,4R)-2,4-bis(3-bromophenoxy)pentane (2.64 g, 6.4 mmol) is azeotropically dried with dry toluene (15 mL×2) and dissolved in dry THF (80 mL). n-Butyl lithium (13.5 mmol, 1.6 M solution in hexane) is added dropwise into the solution at −78° C. within 30 min under N$_2$. After stirring for an additional 1 h at this temperature, chlorodiphenyl phosphine (2.5 mL, 13.5 mmol) in THF (5 mL) is added dropwise to the resulting mixture. The reaction is continued at −78° C. for 1 h and then at RT overnight. The resulting light yellow solution is extracted with DCM/water. The organic phase is separated, washed with water and brine, and dried over anhydrous $Na_2SO_4$. After evaporation of the solvent, a light yellow solid is obtained. The residue is purified by silica gel column chromatography (eluent: EtOAc/hexane=5/100) to give a colorless oily solid. This solid is dissolved in acetone (30 mL), cooled to 0° C., and an aqueous $H_2O_2$ solution (30%, 8.5 mL) is added. The reaction is monitored by thin-layer chromatography. The product is extracted with DCM twice. The combined extract is washed successively with water three times and brine, dried over anhydrous $Na_2SO_4$, and is concentrated in vacuo to give a crude product. Purification by silica gel column chromatography (eluent: EtOAc/ $CHCl_3$/hexane=200/200/20) affords (2R,4R)-2,4-bis[3-(diphenylphosphoryl)phenoxy]-pentane as a colorless solid: $^1$H NMR ($CDCl_3$) 500 MHz δ 1.21–1.23 (d, J=6 Hz, 6H), 1.89–1.92 (t, J=6.3 Hz, 2H), 4.53–4.59 (m, 2H), 6.89–6.92 (m, 2H), 7.02–7.07 (dd, J=12 Hz, 7.5 Hz, 2H), 7.14–7.21 (m, 4H), 7.38–7.64 (m, 20H); $^{31}$P NMR ($CDCl_3$) 202 MHz δ 32.13; $^{13}$C NMR ($CDCl_3$) 125 MHz δ 19.90, 44.36, 70.93, 119.22, 119.31, 119.59, 119.61, 124.23, 124.32, 128.39, 128.49, 129.62, 129.74, 131.92, 131.98, 132.06, 132.72, 133.23, 134.05, 157.87, 157.99; MS (ESI) calcd for $C_{41}H_{38}P_2O_4$ [M]$^+$ 656.7, found 657; HRMS (CI) calcd for $C_{41}H_{38}P_2O_4$ [M+H]$^+$ 657.2324, found 657.1990; [α]$^{20}_D$=−61.0° (c=1, $CHCl_3$).

D. (2R,4R)-2,4-bis[2-Iodo-3-(diphenylphosphoryl)phenoxy]pentane

The title C compound, (2R,4R)-2,4-bis[3-(diphenylphosphoryl)phenoxy]pentane (1.00 g, 1.5 mmol) is azeotropically dried with dry toluene (10 mL×2) and then dissolved in dried THF (20 mL). To this solution is added dropwise a solution of LDA (1.7 mL, 2.0 M) at −78° C. over a period of 30 min. After stirring for an additional 30 min, a solution of diiodoethane (1.20 g, 4.3 mmol) in dried THF (10 mL) is added dropwise into the reaction mixture at −78° C. for over a period of 30 min. The mixture is warmed to RT and the reaction is continued overnight. After evaporation of the solvent with a rotary evaporation, the residue is dissolved in DCM (50 mL). The resulting solution is washed successively with a saturated aqueous ammonium chloride, water and saturated sodium thiosulfate, followed by drying over anhydrous $Na_2SO_4$, and concentration in vacuo to give a crude product. Purification by silica gel column chromatography (eluent: EtOAc/$CHCl_3$/MeOH=200/200/10) affords (2R,4R)-2,4-bis[2-iodo-3-(diphenylphosphoryl)phenoxy]pentane: $^1$H NMR ($CDCl_3$) 500 MHz δ 1.33–1.35 (d, J=6 Hz, 6H), 2.06–2.09 (dd, J=5.5 Hz, 7 Hz, 2H), 4.78–4.83 (m, 2H), 6.55–6.59 (m, 2H), 6.79–6.81 (m, J=8 Hz, 2H), 7.06–7.10 (m, 2H), 7.40–7.70 (m, 20H); $^{31}$P NMR ($CDCl_3$) 202 MHz δ 34.70; MS (ESI) calcd for $C_{41}H_{36}I_2P_2O_4$ [M]$^+$ 908.5, found 909; HRMS (ESI) calcd for $C_{41}H_{36}I_2P_2O_4$ [M+H]+ 909.0257, found 909.0283; [α]$^{20}_D$ =−126.8° (c=1, $CHCl_3$).

E. (S)-[6,6'-(2R,4R-Pentadioxy)]-(2,2')-bis(diphenylphosphoryl)-(1,1')-biphenyl

The title D compound, (2R,4R)-2,4-bis[2-iodo-3-(diphenylphosphoryl)phenoxy]-pentane (0.382 g, 0.42 mmol) is azeotropically dried with dry toluene (10 mL×2) and then added Cu powder (0.215 g, 3.36 mmol) and DMF (5 mL). The resulting mixture is stirred at 140° C. for 12 h under $N_2$. After removal of DMF under reduced pressure, the residue is boiled for a few min with hot $CHCl_3$ (10 mL×3). The insoluble solid is removed by filtration and is washed with hot $CHCl_3$ (5 mL×3). The combined filtrate is washed successively with saturated aqueous ammonium chloride, brine and is dried over anhydrous $Na_2SO_4$. After the solvent is evaporated, the residue is purified by silica gel column chromatography (eluent: $CHCl_3$/MeOH=100/5) to give (S)-[6,6'-(2R,4R-pentadioxy)]-(2,2')-bis(diphenylphosphoryl)-(1,1')-biphenyl as a white solid: $^1$H NMR ($CDCl_3$) 500 MHz δ 1.19–1.21 (d, J=6 Hz, 6H), 1.63–1.65 (t, J=4 Hz, 2H), 4.31–4.36 (m, 2H), 6.81–6.83 (d, J=7.5 Hz, 2H), 6.86–6.90 (dd, J=13.3 Hz, 7.8 Hz, 2H), 7.04–7.14 (m, 6H), 7.22–7.25 (t, J=7.3 Hz, 2H), 7.31–7.35 (m, 8H), 7.40–7.42(t, J=7.5 Hz, 2H), 7.65–7.69 (dd, J=11.5 Hz, 7 Hz, 4H); $^{31}$P NMR ($CDCl_3$) 202 MHz δ 29.29; $^{13}$C NMR ($CDCl_3$) 125 MHz δ 21.84, 40.57, 75.52, 120.52, 120.54, 126.77, 126.86, 127.19, 127.29, 127.80, 127.89, 128.44, 128.55, 130.43, 130.45, 131.00, 132.36, 132.44, 132.54, 133.01, 133.25, 133.69, 134.11, 134.51, 134.94, 156.99, 157.10; MS (ESI) calcd for $C_{41}H_{36}P_2O_4$ [M]$^+$ 654.7, found 655; HRMS (ESI) calcd for $C_{41}H_{36}P_2O_4$ [M+H]$^+$ 655.2168, found 655.2181; [α]$^{20}_D$=+170.00° (c=1, $CHCl_3$).

Alternatively, (S)-[6,6'-(2R,4R-pentadioxy)]-(2,2')-bis(diphenylphosphoryl)-(1,1')-biphenyl may be prepared as follows:

EXAMPLE 2

(S)-[6,6'-(2R,4R-Pentadioxy)]-(2,2')-bis(diphenylphosphoryl)-(1,1')-biphenyl

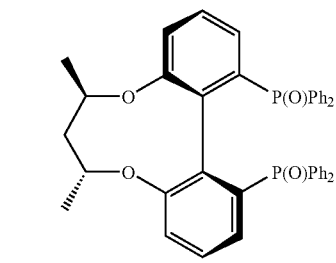

A. (S)-(6,6'-Dihydroxybiphenyl-2,2'-diyl)bis(diphenylphosphine Oxide)

A solution of (S)-(6,6'-methoxybiphenyl-2,2'-diyl)-bis(diphenylphosphine oxide) (1.0 g, 1.6 mmol) in DCM (20 mL) is cooled to −78° C. To this solution is added $BBr_3$ (1.6 g, 6.4 mmol) via a syringe over 30 min. The mixture is stirred at −78° C. for 1 h, and then slowly warmed to RT and stirred overnight. After the mixture is cooled to 0° C., water is added slowly and the aqueous layer is removed via cannula. The organic layer is mixed with methanol and DCM. The resulting solution is dried over anhydrous $Na_2SO_4$ and evaporated to dryness to give the crude product, which is purified by silica gel column chromatography (eluent:$CHCl_3$/MeOH=100/7) to afford (S)-(6,6'-dihydroxybiphenyl-2,2'-diyl)bis(diphenylphosphine oxide) as a white powder: $^1$H NMR (d-DMSO) 500 MHz δ 6.51–6.55 (dd, J=13.8 Hz, 7.3 Hz, 2H), 6.71–6.73 (d, J=8 Hz, 2H), 6.97–7.00 (m, 2H), 7.28–7.55 (m, 20H), 9.00 (s, 1H); $^{31}$P NMR (d-DMSO) 202 MHz δ 29.2; $^{13}$C NMR ($CD_3$OD+ $CD_2Cl_2$) 100 MHz δ 123.83, 129.71, 129.84, 132.50, 132.62, 132.69, 132.85, 135.15, 136.04, 136.19, 136.57, 136.67, 136.78, 136.88, 137.03, 137.13, 138.07, 138.17, 160.08, 160.22; HRMS (EI) calcd for $C_{36}H_{28}P_2O_4$ [M]$^+$ 586.1463, found 586.1439; $[\alpha]^{20}_D$=−80.6° (c=1, 1:1-DCM:MeOH).

B. (S)-[6,6'-(2R,4R-Pentadioxy)]-(2,2')-bis(diphenylphosphoryl)-(1,1')-biphenyl

The title A compound, (S)-(6,6'-dihydroxybiphenyl-2,2'-diyl)bis(diphenylphosphine oxide) (0.403 g, 0.68 mmol) is stirred at RT in DMF (50 mL) in the presence of $K_2CO_3$(0.51 g, 3.70 mmol) for 1 h. To this mixture is added dropwise a solution of the title A compound of Example 1, (2S,4S)-pentanediol-di-p-tosylate (1.135 g, 2.75 mmol) in DMF (30 mL) over a period of 3 h at RT. The reaction is stirred at RT for 12 h and then at 55° C. for 72 h. After the removal of DMF under reduced pressure, the residue is dissolved in DCM. The resulting solution is washed successively with water and brine, followed by drying over anhydrous $Na_2SO_4$ and concentration in vacuo to give a crude product. Purification by silica gel column chromatography (eluent: $CHCl_3$/MeOH=100/5) affords (S)-[6,6'-(2R,4R-pentadioxy)]-(2,2')-bis(diphenylphosphoryl)-(1,1')-biphenyl as a white solid.

EXAMPLE 3

(S)-[6,6'-(2R,4R-Pentadioxy)]-(2,2')-bis(diphenylphosphino)-(1,1')-biphenyl, Ligand A

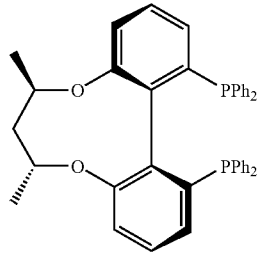

A 100 mL, two-necked flask equipped with a magnetic stirring bar and a reflux condenser is charged with (S)-[6,6'-(2R,4R-pentadioxy)]-(2,2')-bis(diphenylphosphoryl)-(1,1')-biphenyl (620 mg, 0.947 mmol, about 100% diastereomeric excess, de, prepared according to Example 1 or Example 2) and the system is flushed with $N_2$ and azeotropically dried with dry toluene (10 mL×2). Dry and degassed toluene (10 mL), tri-n-butylamine (4.6 mL, 19.0 mmol) and trichlorosilane (2.0 mL, 19.0 mmol) are added to the flask. The mixture is stirred and refluxed overnight. After the solution is cooled to 0° C., a deoxygenated 30% sodium hydroxide solution (30 mL) is added carefully. The resulting mixture is then stirred at 60° C. until the organic and aqueous layers become clear. The organic product is extracted with toluene (10 mL×3, under $N_2$ atmosphere). The extract is washed successively with water (10 mL×2) and brine (10 mL×2), dried over anhydrous $Na_2SO_4$, and concentrated under reduced pressure to give a crude product containing tri-n-butylamine. The crude product is washed with hexane (3 mL×2) to give (S)-[6,6'-(2R,4R-pentadioxy)]-(2,2')-bis(diphenylphosphino)-(1,1')-biphenyl as a white powder: $^1$H NMR (CDCl$_3$) 500 MHz δ 1.22–1.24 (d, J=6.5 Hz, 6H), 1.71–1.72 (t, J=4 Hz, 2H), 4.36–4.42 (m, 2H), 6.67–6.69 (d, J=8 Hz, 2H), 6.82–6.83 (d, J=7.5 Hz, 2H), 7.05–7.20 (m, 12H), 7.30–7.40 (m, 6H), 7.56–7.60 (m, 4H); $^{31}$P NMR (CDCl$_3$) 202 MHz δ −9.88; $^{13}$C NMR (CDCl$_3$) 125 MHz δ 22.03, 40.72, 74.97, 118.03, 127.40, 127.56, 127.58, 128.16, 128.19, 128.22, 128.25, 128.63, 133.47, 133.55, 133.62, 133.81, 133.90, 133.98, 135.43, 135.56, 135.69, 137.38, 137.42, 137.45, 138.51, 138.57, 138.63, 138.70, 157.61, 157.65, 157.70; MS (ESI) calcd for $C_{41}H_{36}P_2O_2$ [M]$^+$ 622.7, found 623; HRMS (ESI) calcd for $C_{41}H_{36}P_2O_2$ [M+H]$^+$623.2269, found 623.2250; $[\alpha]^{20}_D$=+313.8° (c=1, toluene).

EXAMPLE 4

(S)-[6,6'-(2R,5R-Hexadioxy)]-(2,2')-bis(diphenylphosphino)-(1,1')-biphenyl, Ligand B

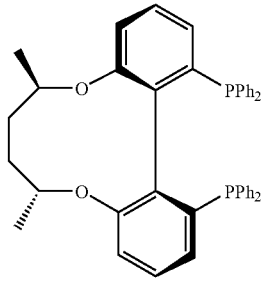

A. (2S,5S)-Hexanediol di-p-tosylate

Under $N_2$ atmosphere and at 0° C., a solution of (2S,5S)-hexanediol (4.0 g, 33.8 mmol) in 20 mL pyridine is added slowly into a mixture of p-toluenesulfonyl chloride (14.20 g, 74.5 mmol) in 30 mL of pyridine over a period of 4 h. The reaction temperature is kept at 0° C. for 2 h, then it is raised to RT and the reaction is continued overnight. The resultant thick mixture is poured into ice-water (500 mL) with vigorous stirring as the product precipitates out. After stirring for 1 h, it is filtered cold and the solid is washed with 500 mL of cold water and air-dried. After drying further in vacuo overnight, the pink crude product is re-crystallized from acetone to afford pure white crystals of (2S,5S)-hexanediol di-p-tosylate:
$^1$H NMR (CDCl$_3$) 500 MHz δ 1.12–1.14 (d, J=6.5 Hz, 6H), 1.48–1.51 (m,2H), 1.56–1.61 (m, 2H), 2.45 (s, 6H), 4.50–4.53 (m, 2H), 7.33–7.35 (d, J=8 Hz, 4H), 7.76–7.78 (d, 8.5 Hz, 4H); $^{13}$C NMR (CDCl$_3$) 125 MHz δ 20.77, 21.58, 31.55, 79.01, 127.65, 129.79, 134.23, 144.65; MS (ESI) calcd for $C_{20}H_{26}S_2O_6$ [M]$^+$ 426.5, found 427; HRMS (ESI) calcd for $C_{20}H_{26}S_2O_6$ [M+Na]$^+$ 449.1068, found 449.1109; calcd for $C_{20}H_{26}S_2O_6$ [M+H]$^+$ 427.1249, found 427.1295; $[\alpha]^{20}_D$=−14.7° (c=1, CHCl$_3$).

B. (S)-[6,6'-(2R,5R-Hexadioxy)]-(2,2')-bis(diphenylphosphoryl)-(1,1')-biphenyl

The title A compound of Example 2, (S)-(6,6'-dihydroxybiphenyl-2,2'-diyl)bis-(diphenylphosphine oxide) (0.500 g, 0.853 mmol) is stirred at RT in DMF (40 mL) in the presence of $K_2CO_3$(0.943 g, 6.823 mmol) for 1 h. A solution of the title A compound, (2S,5S)-hexanediol-di-p-tosylate (1.4558 g, 3.413 mmol) in DMF (40 mL) is added to this mixture over a period of 3 h at RT. The stirring is continued at RT for 24 h and then at 50° C. for 48 h. The DMF is distilled off under reduced pressure. The residue is dissolved in DCM and washed with water and brine successively. The organic solution is dried over anhydrous $Na_2SO_4$ and is concentrated in vacuo to give a crude product which is purified by silica gel column chromatography (eluent: $CHCl_3$/MeOH=100/6) to obtain (S)-[6,6'-(2R,5R-hexadioxy)]-(2,2')-bis(diphenylphosphoryl)-(1,1')-biphenyl as a white solid: $^1$H NMR ($CDCl_3$) 500 MHz δ 0.97–0.98 (d, J=6 Hz, 6H), 1.15–1.17 (d, J=10 Hz, 2H), 1.71–1.73 (d, J=9 Hz, 2H), 4.42–4.49 (m, 2H), 6.79–6.84 (dd, J=13.5 Hz, 7.5 Hz, 2H), 6.88–6.89 (d, J=8 Hz, 2H), 7.11–7.15 (m, 2H), 7.20–7.23 (m, 4H), 7.32–7.38 (m, 6H), 7.41–7.45 (m, 6H), 7.72–7.76 (dd, J=11.8 Hz, 7.3 Hz, 4H); $^{31}$P NMR 202 MHz δ 30.03; $^{13}$C NMR 125 MHz δ 18.65, 25.63, 75.61, 118.90, 125.88, 125.98, 127.31, 127.40, 127.80, 127.89, 128.05, 130.49, 130.51, 130.94, 132.27, 132.35, 132.55, 132.63, 132.78, 133.36, 133.65, 133.88, 134.19, 134.71, 155.83, 155.93; MS (ESI) calcd for $C_{42}H_{38}P_2O_4$ [M]$^+$ 668.7, found 669; HRMS (ESI) calcd for $C_{42}H_{38}P_2O_4$ [M+H]$^+$ 669.2324, found 669.2251; $[α]^{20}_D$=+76.0° (c, 1, $CHCl_3$).

C. (S)-[6,6'-(2R,5R-Hexadioxy)]-(2,2')-bis(diphenylphosphino)-(1,1')-biphenyl

A 100 mL, two-necked flask equipped with a magnetic stirring bar and a reflux condenser is charged with the title B compound, (S)-[6,6'-(2R,5R-hexadioxy)]-(2,2')-bis(diphenylphosphoryl)-(1,1')-biphenyl (509 mg, 0.761 mmol, about 100% de) and system is flushed with $N_2$ gas and is azeotropically dried with dry toluene (10 mL×2). Under $N_2$ atmosphere dry and degassed toluene (10 mL), tri-n-butylamine (3.64 mL, 15.3 mmol) and trichlorosilane (1.54 mL, 15.3 mmol) are added to the flask by means of syringe. The mixture is stirred and refluxed overnight. After the solution is cooled to 0° C., a 30% aqueous sodium hydroxide solution (23 mL) is carefully added. The mixture is then stirred at 60° C. until the organic and aqueous layers become clear. The organic product is extracted with toluene (10 mL×3, under nitrogen atmosphere) and the extract is washed successively with water (10 mL×2), brine (10 mL×2) and dried over anhydrous $Na_2SO_4$. The organic layer is concentrated under reduced pressure to give a crude product containing tri-n-butylamine. It is washed with hexane (2 mL×3) to give (S)-[6,6'-(2R,5R-hexadioxy)]-(2,2')-bis(diphenylphosphino)-(1,1')-biphenyl as light yellow needles: $^1$H NMR ($CDCl_3$) 500 MHz δ 0.99–1.00 (d, J=6.5 Hz, 6H), 1.17–1.20 (d, J=10.5 Hz, 2H), 1.73–1.75 (d, J=9 Hz, 2H), 4.33–4.41 (m, 2H), 6.61–6.63 (d, J=7.5 Hz, 2H), 6.75–6.76 (d, J=8.5 Hz, 2H), 7.09–7.17 (m, 12H), 7.24–7.26 (m, 6H), 7.38–7.41 (m,4H); $^{31}$P NMR 202 MHz δ −10.75; $^{13}$C NMR 125 MHz δ 19.28, 27.17, 75.82, 115.75, 126.42, 127.50, 127.52, 127.55, 127.60, 127.92, 128.10, 128.12, 128.14, 128.45, 133.60, 133.69, 133.77, 133.82, 133.91, 133.99, 134.88, 135.02, 135.16, 137.46, 137.50, 137.55, 138.62, 138.67, 138.74, 139.23, 139.25, 139.27, 156.41, 156.46, 156.50; MS (ESI) calcd for $C_{42}H_{38}P_2O_2$ [M]$^+$ 636.7, found 637; HRMS (ESI) calcd for $C_{42}H_{38}P_2O_2$ [M+H]$^+$ 637.2425, found 637.2402; $[α]^{20}_D$=+243.5° (c=1, toluene).

EXAMPLE 5

(R)-[6,6'-(2S,3S-Butadioxy)]-(2,2')-bis(diphenylphosphino)-(1,1')-biphenyl, Ligand C

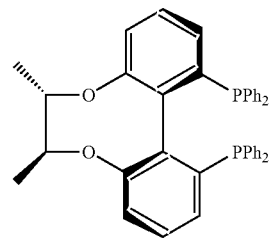

A. (2R,3R)-Butanediol Dimesylate

Under $N_2$ atmosphere and at 0° C., a solution of (2R,3R)-butanediol (3.0 g, 33.3 mmol) in 30 mL pyridine is added slowly into a mixture of methanesulfonyl chloride (14.20 g, 74.5 mmol) in 30 mL of pyridine over a period of 1 h. The reaction temperature is kept at 0° C. for 2 h, then it is raised to RT and the reaction is continued overnight. The resultant thick mixture is poured into ice-water (500 mL) with vigorous stirring as the product precipitated out. After stirring for 1 h, it is filtered cold and the solid is washed with 500 mL of cold water and air-dried. After drying further in vacuo overnight, the white crude product is re-crystallized from acetone to afford pure colorless monoclinic crystals of (2R,3R)-butanediol dimesylate: $^1$H NMR ($CDCl_3$) 500 MHz δ 1.45–1.46 (d, J=6.5 Hz, 6H), 3.07 (s, 6H), 4.74–4.80 (m, 2H); $^{13}$C NMR ($CDCl_3$) 125 MHz δ 17.25, 38.79, 78.66; MS (ESI) calcd for $C_6H_{14}S_2O_6$ [M]$^+$ 246.3, found 247; HRMS (ESI) calcd for $C_6H_{14}S_2O_6$ [M+Na]$^+$ 269.0129, found 269.0187; calcd for $C_6H_{14}S_2O_6$ [M+H]$^+$ 247.0310, found 247.0372; $[α]^{20}_D$=1.3° (c=1, $CHCl_3$).

B. (R)-(6,6'-Dihydroxybiphenyl-2,2'-diyl)bis(diphenylphosphine oxide)

A solution of (R)-(6,6'-methoxybiphenyl-2,2'-diyl)-bis(diphenylphosphine oxide) (1 g, 1.63 mmol) in DCM (20 mL) is cooled to −78° C. To this solution is added $BBr_3$ (1.6 g, 6.4 mmol) via a syringe over a period of 30 min. The mixture is stirred at −78° C. for 1 h, and then slowly warmed to RT and stirred overnight. After the mixture is cooled to 0° C., water is added slowly and the aqueous layer is removed via cannula. The organic layer is mixed with methanol and DCM. The resulting solution is dried over anhydrous $Na_2SO_4$ and evaporated to dryness to give the crude product, which is purified by silica gel column chromatography (eluent:$CHCl_3$/MeOH=100/7) to afford (R)-(6,6'-hydroxybiphenyl-2,2'-diyl)-bis(diphenylphosphine oxide) as a white powder: $^1$H NMR (d-DMSO) 500 MHz δ 6.52–6.56 (dd, J=13.3 Hz, 8.3 Hz, 2H), 6.72–6.74 (d, J=8 Hz, 2H), 6.97–7.01 (m, 2H), 7.28–7.56 (m, 20H), 9.01 (s, 1H); $^{31}$P NMR (d-DMSO) 202 MHz δ 29.2; $^{13}$C NMR ($CD_3OD$+$CD_2Cl_2$ 100 MHz δ 123.99, 129.80, 129.92, 132.50, 132.53, 132.62, 132.66, 132.83, 135.07, 136.04, 136.55, 136.65, 136.78, 136.88, 137.00, 137.23, 138.04, 138.27, 160.12, 160.26; HRMS (ESI) calc. for $C_{36}H_{28}P_2O_4$ [M+H]$^+$ 587.1541, found 587.1530; $[α]^{20}_D$=80.2° (c=1, 1:1-DCM:MeOH).

C. (R)-[6,6'-(2S,3S-Butadioxy)]-(2,2')-bis(diphenylphosphoryl)-(1,1')-biphenyl

The title B compound, (R)-(6,6'-dihydroxybiphenyl-2,2'-diyl)bis(diphenylphosphine oxide) (1.100 g, 1.877 mmol) is stirred at RT in DMF (100 mL) in the presence of $K_2CO_3$ (3.113 g, 22.525 mmol) for 1 h. A DMF (50 mL) solution of the title A compound, (2R,3R)-butanediol-dimesylate (2.774 g, 11.263 mmol) is added to this mixture over a period of 3 h at RT. The reaction is stirred at 60° C. for 48 h. DMF is distilled off under reduced pressure. The residue is dissolved in DCM and washed with water and brine successively. The organic solution is dried over anhydrous $Na_2SO_4$ and is concentrated in vacuo to give a crude product which is purified by silica gel column chromatography (eluent: $CHCl_3$/MeOH=100/5) to obtain (R)-[6,6'-(2S,3S-butadioxy)]-(2,2')-bis(diphenylphosphoryl)-(1,1')-biphenyl as a white solid: $^1$H NMR (CDCl$_3$) 500 MHz δ 1.25–1.27 (d, J=6 Hz, 6H), 3.65–3.71 (m, 2H), 6.84–6.85 (d, J=7.5 Hz, 2H), 6.93–6.97 (m, 2H), 7.08–7.13 (m, 6H) 7.21–7.24 (m, 2H), 7.27–7.34 (m, 8H), 7.37–7.40 (m, 2H), 7.63–7.67 (m, 4H); $^{31}$P NMR 202 MHz δ 28.46; $^{13}$C NMR 125 MHz δ 18.97, 86.33, 123.80, 123.82, 127.16, 127.26, 127.66, 127.76, 127.79, 127.87, 129.34, 129.46, 130.20, 130.22, 130.74, 130.76, 131.97, 132.04, 132.33, 132.40, 132.92, 133.65, 133.76, 134.49, 134.72, 135.56, 158.97, 159.08; MS (ESI) calcd for $C_{40}H_{34}P_2O_4$ [M]$^+$ 640.6, found 641; HRMS (ESI) calcd for $C_{40}H_{34}P_2O_4$ [M+H]$^+$ 641.2011, found 641.1991; $[\alpha]^{20}_D$=−197.4° (c=1, CHCl$_3$).

D. (R)-[6,6'-(2S,3S-Butadioxy)]-(2,2')-bis(diphenylphosphino)-(1,1')-biphenyl

A 100 mL, two-necked flask equipped with a magnetic stirring bar and a reflux condenser is charged with the title C compound, (R)-[6,6'-(2S,3S-butadioxy)]-(2,2')-bis(diphenylphosphoryl)-(1,1')-biphenyl (480 mg, 0.749 mmol, 100% de) and system is flushed with $N_2$ gas and azeotropically dried with dry toluene (10 mL×2). Under $N_2$ atmosphere dry and degassed toluene (10 mL), tri-n-butylamine (3.7 mL, 15.5 mmol) and trichlorosilane (1.6 mL, 15.5 mmol) are added to the flask by means of syringe. The mixture is stirred at reflux overnight. After the solution is cooled to 0° C., a 30% aqueous sodium hydroxide solution (23 mL) is carefully added. The mixture is then stirred at 60° C. until the organic and aqueous layers become clear. The organic product is extracted with toluene (10 mL×3, under nitrogen atmosphere) and the extract is washed successively with water (10 mL×2), brine (10 mL×2) and dried over anhydrous $Na_2SO_4$. The organic layer is concentrated under reduced pressure to give a crude product containing tri-n-butylamine. It is washed with hexane (3×2 mL) to give (R)-[6,6'-(2S,3S-butadioxy)]-(2,2')-bis(diphenylphosphino)-(1,1')-biphenyl as a white powdery solid: $^1$H NMR (CDCl$_3$) 500 MHz δ 1.27–1.28 (d, J=6 Hz, 6H), 3.71–3.78 (m, 2H), 6.79–6.81 (d, J=7.5 Hz, 2H), 6.88–6.90 (d, J=8 Hz, 2H), 7.01–7.04 (m, 4H), 7.13–7.19 (m, 8H), 7.35–7.38 (m, 6H), 7.58–7.61 (m, 4H); $^{31}$P NMR 202 MHz δ −8.42; $^{13}$C NMR 125 MHz δ 19.09, 86.33, 122.20, 127.74, 127.76, 127.78, 128.24, 128.26, 128.96, 129.50, 133.21, 133.29, 133.38, 133.87, 133.96, 134.05, 135.08, 135.20, 135.32, 137.39, 137.42, 137.46, 138.33, 138.40, 138.46, 138.57, 138.60, 138.63, 159.69, 159.72, 159.75; MS (ESI) calcd for $C_{40}H_{34}P_2O_2$ [M]$^+$ 608.6, found 609. HRMS (ESI) calcd for $C_{40}H_{34}P_2O_2$ [M+H]$^+$ 609.2113, found 609.2089; $[\alpha]^{20}_D$=−341.6° (c=1, toluene).

EXAMPLE 6

Preparation of RuLCl$_2$(DMF)$_n$ Catalysts

A Schlenk tube with a magnetic stirring bar is charged with [RuCl$_2$(benzene)]$_2$ (2.0 mg, 4×10$^{-3}$ mmol, Kitamora et al., *Org. Synth.* 1993, 71, 1), the ligand [Ligand A, 5.3 mg; Ligand B, 5.2 mg; Ligand C, 5.4 mg; (S)-MeO-BIPHEP 4.9 mg or (S)-BINAP 5.3 mg; 8.4×10$^{-3}$ mmol] and degassed dry DMF (2.0 mL). The resulting solution is heated at 100° C. for 30 min and then concentrated in vacuo to give the catalyst as a reddish-brown solid.

EXAMPLE 7

Preparation of Ru[L(p-cymene)Cl]Cl Catalysts

To a mixture of the ligand [Ligand A, 8.6 mg; Ligand B, 8.8 mg; Ligand C, 8.4 mg; (S)-MeO-BIPHEP 8.1 mg or (S)-BINAP 8.6 mg; 1.38×10$^{-2}$ mmol] and [Ru(p-cymene)Cl$_2$]$_2$ (3.7 mg, 6.0×10$^{-3}$ mmol, Mashima et al., *J. Org. Chem.* 1994, 59, 3064) in a Schlenk tube is added ethanol (3.0 mL) and DCM (1.0 mL). The resulting mixture is stirred at 50° C. for 1 h and is filtered. The orange yellow filtrate is concentrated in vacuo to give the catalyst as an orange solid.

$^{31}$P NMR (CDCl$_3$) 202 MHz:

Ru[Ligand A (p-cymene)Cl]Cl: δ 28.90 (d, J=64.4 Hz), 43.00 (d, J=64.4 Hz).

Ru[Ligand B (p-cymene)Cl]Cl: δ 28.74 (d, J=63.8 Hz), 42.63 (d, J=63.8 Hz).

Ru[Ligand C (p-cymene)Cl]Cl: δ 30.26 (d, J=65.8 Hz), 44.19 (d, J=65.8 Hz).

EXAMPLE 8

Asymmetric Hydrogenation of β-Ketoesters

A glass-lined stainless steel autoclave is charged with β-ketoester (0.5 mmol), RuLCl$_2$(DMF)$_n$ (7.5×10$^{-4}$ mmol), DCM (12.5 μL) and methanol or ethanol (987.5 μL) under $N_2$ atmosphere. The mixture is stirred well with a magnetic stirrer at a certain temperature under 50 psi H$_2$. Conversions of the substrate and enantiomeric excesses of the products are determined by GC after converting the products to the corresponding acetyl derivatives or by HPLC.

After the catalytic reaction is completed, the organic solvent is removed in vacuo. To a one-necked flask with a magnetic stirring bar is charged with the crude product, dry pyridine (0.5 mL) and acetic anhydride (0.5 mL). The suspension is stirred at RT for 3 h. To the mixture is added ethyl acetate (5.0 mL) and aqueous HCl (20%, 5 mL) at 0° C. The organic solution is washed with water (10 mL×2), dried over anhydrous $Na_2SO_4$, and is concentrated in vacuo to give a crude product. Purification by column chromatography (silica gel; eluent: hexane/EtOAc=1/1) affords the pure product.

EXAMPLE 9

Asymmetric Hydrogenation of 2-(6'-Methoxy-2'-naphthyl)propenoic Acid

A glass-lined stainless steel reactor is charged with 5.0 mg of 2-(6'-methoxy-2'-naphthyl)propenoic acid, 2.2×10$^{-4}$ mmol of Ru[L(p-cymene)Cl]Cl catalyst and 2.5 mL of methanol. The solution is stirred well with a magnetic stirrer at a certain temperature under a chosen hydrogen pressure.

Conversion of the substrate and enantiomeric excess of the product are determined by HPLC with a Sumichiral OA-2500 column.

What is claimed is:

1. A compound of the formula

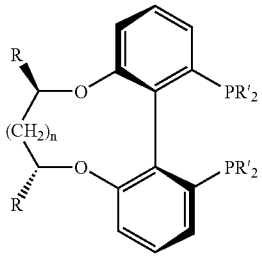

(I)

wherein
R is optionally substituted lower alkyl, cycloalkyl or aryl;
R' is alkyl or aryl;
n is zero or an integer of 1 or 2;
or an enantiomer thereof; or an enantiomeric mixture thereof.

2. A compound according to claim 1, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

3. A compound according to claim 2, wherein
R is methyl;
or an enantiomer thereof; or an enantiomeric mixture thereof.

4. A catalyst comprising a transition metal bound to a compound of the formula

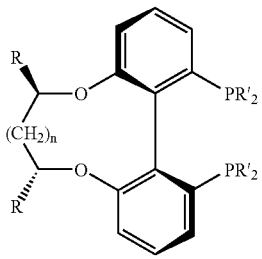

(I)

wherein
R is optionally substituted lower alkyl, cycloalkyl or aryl;
R' is alkyl or aryl;
n is zero or an integer of 1 or 2;
or an enantiomer thereof; or an enantiomeric mixture thereof.

5. A catalyst according to claim 4, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

6. A catalyst according to claim 5, wherein
R is methyl;
or an enantiomer thereof; or an enantiomeric mixture thereof.

7. A catalyst according to claim 4, wherein the transition metal is selected from the group consisting of copper, iridium, nickel, palladium, platinum, rhodium and ruthenium.

8. A catalyst according to claim 7, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

9. A catalyst according to claim 8, wherein
R is methyl;
or an enantiomer thereof; or an enantiomeric mixture thereof.

10. A catalyst according to claim 9, wherein the transition metal is ruthenium or rhodium.

11. A method for preparing a compound of the formula

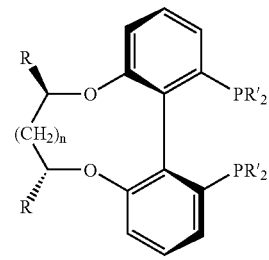

(I)

wherein R is optionally substituted lower alkyl, cycloalkyl or aryl; R' is alkyl or aryl; and n is zero or an integer of 1 or 2; or an enantiomer thereof; or an enantiomeric mixture thereof; which method comprises:

(a) reacting a phenol of the formula

(II)

wherein X is chloro, bromo or iodo; with an alkylating agent of the formula

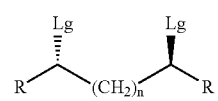

(III)

wherein Lg represents a leaving group; and R and n have meanings as defined for formula (I); or an enantiomer thereof; or an enantiomeric mixture thereof; in the presence of a base and an inert organic solvent to afford a compound of the formula

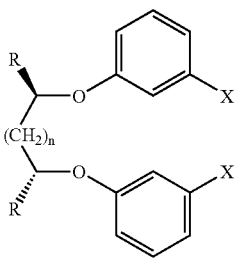
(IV)

wherein R, n and X have meanings as defined above; or an enantiomer thereof; or an enantiomeric mixture thereof;

(b) dehalogenating a compound of formula (IV) in an inert organic solvent, and treating the resulting dianion with a phosphine chloride of the formula $R'_2PCl$     (V)

wherein R' is alkyl or aryl; to afford a compound of the formula

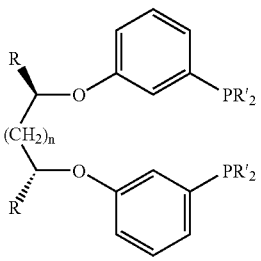
(VI)

wherein R, n and R' have meanings as defined above; or an enantiomer thereof; or an enantiomeric mixture thereof;

(c) treating a compound of formula (VI) with an oxidizing agent to afford a compound of the formula

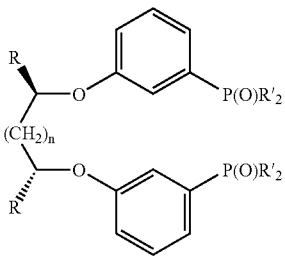
(VII)

wherein R, n and R' have meanings as defined above; or an enantiomer thereof; or an enantiomeric mixture thereof;

(d) deprotonating a compound of formula (VII) in an inert organic solvent, and treating the resulting dianion with an iodine source to afford a compound of the formula

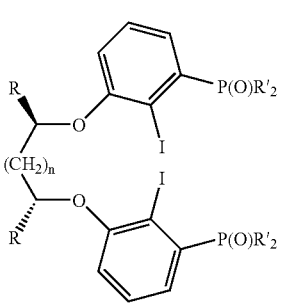
(VIII)

wherein R, n and R' have meanings as defined above; or an enantiomer thereof; or an enantiomeric mixture thereof;

(e) treating a compound of formula (VIII) with copper in an inert organic solvent to afford a compound of the formula

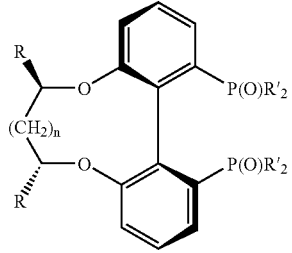
(IX)

wherein R, n and R' have meanings as defined above; or an enantiomer thereof; or an enantiomeric mixture thereof; and (f) treating a compound of formula (IX) with a reducing agent in an inert organic solvent to afford a compound of formula (I) wherein R, n and R' have meanings as defined above; or an enantiomer thereof; or an enantiomeric mixture thereof.

12. A method according to claim 11, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

13. A method according to claim 12, wherein
R is methyl;
or an enantiomer thereof; or an enantiomeric mixture thereof.

14. A method for preparing a compound of the formula

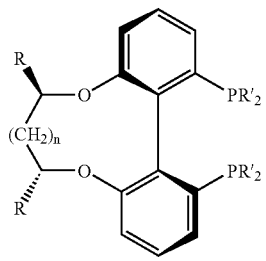
(I)

wherein R is optionally substituted lower alkyl, cycloalkyl or aryl; R' is alkyl or aryl; and n is zero or an integer of 1 or 2; or an enantiomer thereof; or an enantiomeric mixture thereof; which method comprises:

(a) treating a compound of the formula

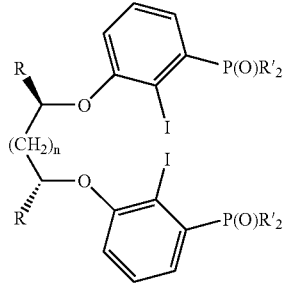
(VIII)

wherein R, n and R' have meanings as defined for formula (I); with copper in an inert organic solvent to afford a compound of the formula

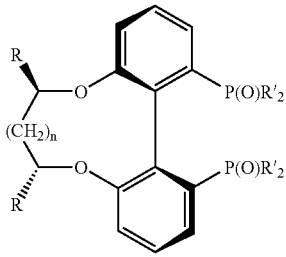
(IX)

wherein R, n and R' have meanings as defined above; or an enantiomer thereof; or an enantiomeric mixture thereof; and (b) treating a compound of formula (IX) with a reducing agent in an inert organic solvent to afford a compound of formula (I) wherein R, n and R' have meanings as defined above; or an enantiomer thereof; or an enantiomeric mixture thereof.

15. A method according to claim 14, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

16. A method according to claim 15, wherein
R is methyl;
or an enantiomer thereof; or an enantiomeric mixture thereof.

17. A method for preparing a compound of the formula

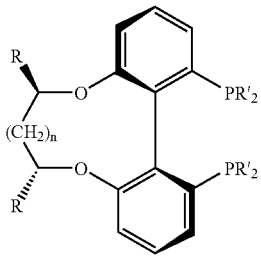
(I)

wherein R is optionally substituted lower alkyl, cycloalkyl or aryl; R' is alkyl or aryl; and n is zero or an integer of 1 or 2; or an enantiomer thereof; or an enantiomeric mixture thereof; which method comprises:

(a) reacting a compound of the formula

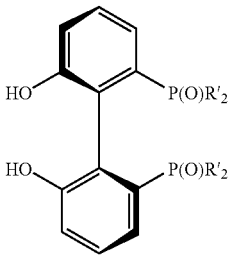
(X)

wherein R' has a meaning as defined for formula (I); or an enantiomer thereof; or an enantiomeric mixture thereof; with an alkylating agent of the formula

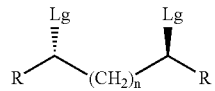
(III)

wherein Lg represents a leaving group; and R and n have meanings as defined for formula (I); or an enantiomer thereof; or an enantiomeric mixture thereof; in the presence of a base and an inert organic solvent to afford a compound of the formula

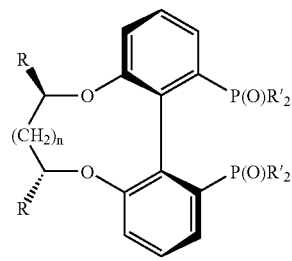
(IX)

wherein R, n and R' have meanings as defined above; or an enantiomer thereof; or an enantiomeric mixture thereof; and (b) treating a compound of formula (IX) with a reducing agent in an inert organic solvent to afford a compound of formula (I) wherein R, n and R' have meanings as defined above; or an enantiomer thereof; or an enantiomeric mixture thereof.

18. A method according to claim 17, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

19. A method according to claim 18, wherein
R is methyl;
or an enantiomer thereof; or an enantiomeric mixture thereof.

20. A method for converting a prochiral substrate to a chiral product by an asymmetric reaction in the presence of a catalyst comprising a transition metal bound to a compound of the formula

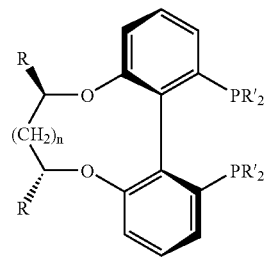
(I)

wherein
R is optionally substituted lower alkyl, cycloalkyl or aryl;
R' is alkyl or aryl;
n is zero or an integer of 1 or 2;
or an enantiomer thereof; or an enantiomeric mixture thereof.

21. A method according to claim 20, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

22. A method according to claim 21, wherein
R is methyl;
or an enantiomer thereof; or an enantiomeric mixture thereof.

23. A method according to claim 20, wherein the transition metal is selected from the group consisting of copper, iridium, nickel, palladium, platinum, rhodium and ruthenium.

24. A method according to claim 23, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

25. A method according to claim 24, wherein
R is methyl;
or an enantiomer thereof; or an enantiomeric mixture thereof.

26. A method according to claim 25, wherein the transition metal is ruthenium or rhodium.

27. A method according to claim 20, wherein the asymmetric reaction is selected from the group consisting of catalytic hydrogenation, hydrosilylation, hydroboration, hydroformylation, hydrocarboxylation, hydroacylation, Heck reaction, allylic isomerization and allylic substitution.

28. A method according to claim 27, wherein the transition metal is selected from the group consisting of copper, iridium, nickel, palladium, platinum, rhodium and ruthenium.

29. A method according to claim 28, wherein
R is methyl, ethyl, n-propyl, i-propyl, n-butyl, i-butyl, neopentyl, cyclopropyl, benzyl or phenyl;
R' is phenyl;
n is zero or an integer of 1 or 2;
or an enantiomer thereof; or an enantiomeric mixture thereof.

30. A method according to claim 29, wherein
R is methyl;
or an enantiomer thereof; or an enantiomeric mixture thereof.

31. A method according to claim 30, wherein the transition metal is ruthenium or rhodium.

32. A method according to claim 31, wherein the asymmetric reaction is catalytic hydrogenation.

33. A method according to claim 32, wherein the prochiral substrate is a ketone.

34. A method according to claim 33, wherein the prochiral substrate is a $\alpha$- or $\beta$-ketoester.

35. A method according to claim 32, wherein the prochiral substrate is an activated carbon-carbon double bond.

* * * * *